(12) United States Patent
Okazaki et al.

(10) Patent No.: US 9,707,187 B2
(45) Date of Patent: *Jul. 18, 2017

(54) COMPOSITION FOR ENHANCING TRANSDERMAL ABSORPTION OF A DRUG AND PATCH PREPARATION

(75) Inventors: Arimichi Okazaki, Osaka (JP);
Tsuyoshi Mukobata, Osaka (JP);
Sachiko Sakamoto, Osaka (JP);
Akinori Hanatani, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/611,154

(22) Filed: Sep. 12, 2012

(65) Prior Publication Data

US 2013/0064868 A1 Mar. 14, 2013

(30) Foreign Application Priority Data

Sep. 13, 2011 (JP) ................................ 2011-200023

(51) Int. Cl.
| A61K 47/10 | (2006.01) |
| A61K 9/00 | (2006.01) |
| A61K 47/18 | (2006.01) |
| A61K 9/70 | (2006.01) |
| A61K 31/405 | (2006.01) |
| A61K 31/41 | (2006.01) |
| A61K 31/422 | (2006.01) |
| A61K 31/565 | (2006.01) |

(52) U.S. Cl.
CPC .......... *A61K 9/7038* (2013.01); *A61K 9/7084* (2013.01); *A61K 31/405* (2013.01); *A61K 31/41* (2013.01); *A61K 31/422* (2013.01); *A61K 31/565* (2013.01); *A61K 9/0014* (2013.01)

(58) Field of Classification Search
None
See application file for complete search history.

(56) References Cited

U.S. PATENT DOCUMENTS

| 5,891,462 | A | 4/1999 | Carrara |
| 6,635,674 | B1 | 10/2003 | Kaneko et al. |
| 2005/0255149 | A1* | 11/2005 | Narui et al. .................. 424/448 |
| 2006/0153905 | A1 | 7/2006 | Carrara et al. |
| 2007/0269379 | A1* | 11/2007 | Mitragotri et al. ............ 424/9.2 |
| 2008/0233183 | A1 | 9/2008 | McCook et al. |
| 2009/0068252 | A1 | 3/2009 | Amano et al. |
| 2009/0117192 | A1 | 5/2009 | Ah et al. |
| 2009/0181954 | A1 | 7/2009 | Sharma et al. |
| 2009/0264806 | A1 | 10/2009 | Tamura et al. |
| 2010/0137429 | A1 | 6/2010 | Yoneda et al. |
| 2010/0210613 | A1 | 8/2010 | Matsui et al. |
| 2010/0256174 | A1 | 10/2010 | Yamaguchi et al. |
| 2010/0273895 | A1 | 10/2010 | Stinchcomb et al. |
| 2011/0190714 | A1 | 8/2011 | Oda et al. |
| 2012/0004306 | A1* | 1/2012 | Miura et al. .................. 514/567 |

FOREIGN PATENT DOCUMENTS

| CN | 101909651 | 12/2010 |
| EP | 0 359 625 | 3/1990 |
| EP | 0 417 496 A2 | 3/1991 |
| EP | 0 811 381 | 12/1997 |
| EP | 1 142 588 | 10/2001 |
| GB | 1 518 683 | 7/1978 |
| JP | 01-308225 | 12/1989 |
| JP | 09-143062 | 11/1995 |
| JP | 8-133979 | 5/1996 |
| JP | 10-72351 | 3/1998 |
| JP | 2000-143540 | 5/2000 |
| JP | 2001-302503 | 10/2001 |
| JP | 2006-22057 | 1/2006 |
| JP | 2007-508261 | 4/2007 |
| JP | 2009-275040 | 11/2009 |
| JP | 2011-51986 | 3/2011 |
| JP | 2011-507904 | 3/2011 |
| WO | 00/53226 | 9/2000 |
| WO | 2008/012071 | 1/2008 |
| WO | 2009/037813 | 3/2009 |

(Continued)

OTHER PUBLICATIONS

European Search Report issued Jan. 2, 2013 in corresponding European Application No. 12184298.3.
Cheong et al., "Effect of ethanolamine salts and enhancers on the percutaneous absorption of piroxicam from a pressure sensitive adhesive matrix", European Journal of Pharmaceutical Sciences, vol. 18, pp. 149-153, 2003.
Notice of Reasons for Refusal mailed Apr. 7, 2015 in corresponding Japanese Application No. 200023/2011 with English translation.
State Intellectual Property Office of the People's Republic of China Office Action issued Jul. 2, 2015 in the corresponding Chinese Application No. 201210340114.1 with English translation.
State Intellectual Property Office of the People's Republic of China Office Action issued Mar. 4, 2016 in the corresponding Chinese Application No. 201210340114.1 with English translation.

(Continued)

*Primary Examiner* — Robert A Wax
*Assistant Examiner* — Randeep Singh
(74) *Attorney, Agent, or Firm* — Wenderoth, Lind & Ponack, L.L.P.

(57) ABSTRACT

The problem of the present invention is to provide a composition for enhancing transdermal absorption of a drug, which shows a sufficiently high enhancing effect on transdermal absorption of a drug, particularly, a composition for enhancing transdermal absorption of a drug, which shows a sufficiently high enhancing effect on transdermal absorption of an acidic drug.
A composition for enhancing transdermal absorption of a drug, comprising an unsaturated higher alcohol having 12-20 carbon atoms and a polyvalent alcohol having 3-8 carbon atoms. A composition for enhancing transdermal absorption of a drug, comprising an unsaturated higher alcohol having 12-20 carbon atoms, a polyvalent alcohol having 3-8 carbon atoms and an organic amine having 2-9 carbon atoms.

8 Claims, 1 Drawing Sheet

(56) References Cited

FOREIGN PATENT DOCUMENTS

| WO | 2009/066457 | 5/2009 |
|---|---|---|
| WO | 2010/103845 | 9/2010 |
| WO | 2010/113225 | 10/2010 |

OTHER PUBLICATIONS

Notice of Opposition against Patent received May 23, 2016 in corresponding Japanese Application No. 5820207 with English translation.
Notice of Forwarding A Duplicate of Notice of Opposition mailed on Jun. 29, 2016 with English translation.
Reference Material 1 dated May 17, 2016, print out of http://www.maruho.co.jp/medical/academic/infostore/vol02/03.html, partial English translation.
Notice of Reasons for Revocation mailed Aug. 15, 2016 in corresponding Japanese Patent No. 5820207 with English translation.
Office Action issued Jul. 4, 2016 in corresponding European Application No. 12 184 298.3.
Office Action issued Jul. 4, 2016 in corresponding European Application No. 12 184 301.5.
Decision of Opposition issued Feb. 23, 2017 in corresponding Japanese Patent No. 5820207, with English translation, Opposition No. 700481/2016.
Notice of Forwarding a Duplicate of Opponent's Arguments issued Feb. 23, 2017 in corresponding Japanese Patent No. 5820207, with English translation, Opposition No. 700481/2016.
Opponent's Arguments issued Dec. 8, 2016 in corresponding Japanese Patent No. 5820207, with English translation, Opposition No. 700481/2016.

* cited by examiner

COMPOSITION FOR ENHANCING TRANSDERMAL ABSORPTION OF A DRUG AND PATCH PREPARATION

TECHNICAL FIELD OF THE INVENTION

The present invention relates to a composition for enhancing transdermal absorption of a drug, which shows a sufficiently high enhancing effect on transdermal absorption to of a drug.

BACKGROUND OF THE INVENTION

Transdermal absorption preparation has many advantages in that the first pass effect in the liver or gastrointestinal tract can be avoided, a stable blood concentration can be maintained during adhesion since the drug is absorbed from the skin over a long period, administration can be discontinued when side effects are expressed and the like. However, since many drugs show low skin permeability, there are not many drugs actually formulated into transdermal absorption preparations, and a technique for improving transdermal absorbability of a drug has been desired.

Various methods have heretofore been considered to improve transdermal absorbability of a drug. As one of them, an attempt has been made to appropriately design a solution used for dissolving a drug to improve transdermal absorbability of the drug. For example, WO2009/066457 teaches that an external preparation composition comprising a fatty acid ionic liquid as an active ingredient improves transdermal absorbability of the drug. To be specific, in WO2009/066457, a fatty acid having 5-20 carbon atoms, an organic amine having 4-12 carbon atoms, ethanol and isopropanol, which are lower alcohols, and propylene glycol, which is a polyvalent alcohol, are used for external preparation compositions. Moreover, WO00/53226 shows that a composition containing a higher alcohol having 8-12 carbon atoms and a polyvalent alcohol improves transdermal absorbability of a drug.

However, according to the study of the present inventors, such compositions that allegedly improve transdermal absorbability of conventional drugs fail to provide stable transdermal absorbability since volatilization of solvent changes the composition, or fail to provide a transdermal absorption preparation that expresses an expected pharmacological effect since skin permeation amount of drug cannot be sufficiently increased, or show a transdermal absorption enhancing effect only for a particular drug, and none of them showed a sufficiently superior absorption enhancing effect and broad utility. To markedly improve transdermal absorbability of a drug, therefore, a more drastic improvement of the composition for enhancing transdermal absorption of a drug is necessary.

SUMMARY OF THE INVENTION

The present invention has been made in view of the above-mentioned situation and aims to provide a composition for enhancing transdermal absorption, which shows a sufficiently high enhancing effect on transdermal absorption of a drug, particularly, a composition for enhancing transdermal absorption of a drug, which shows a sufficiently high enhancing effect on transdermal absorption of an acidic drug.

In addition, it aims to provide a patch preparation showing sufficiently high transdermal absorbability of a drug, particularly a patch preparation showing sufficiently high transdermal absorbability of an acidic drug.

The present inventors have conducted intensive studies in an attempt to solve the aforementioned problems and found a combination of an unsaturated higher alcohol having 12-20 carbon atoms and a polyvalent alcohol having 3-8 carbon atoms extremely advantageously acts on the improvement of transdermal absorbability of a drug, and that further combination of an organic amine having 2-9 carbon atoms with such unsaturated higher alcohol and polyvalent alcohol markedly improves transdermal absorbability of, particularly, an acidic drug. They have conducted further studies based on the above findings, and completed the present invention.

Accordingly, the gist of the present invention is as follows.

[1] A composition for enhancing transdermal absorption of a drug, comprising an unsaturated higher alcohol having 12-20 carbon atoms and a polyvalent alcohol having 3-8 carbon atoms.

[2] The composition of the above-mentioned [1], wherein the unsaturated higher alcohol having 12-20 carbon atoms is a straight chain alcohol.

[3] The composition of the above-mentioned [1], wherein the unsaturated higher alcohol having 12-20 carbon atoms contains oleyl alcohol.

[4] The composition of any one of the above-mentioned [1] to [3], wherein the polyvalent alcohol having 3-8 carbon atoms is one or more kinds selected from the group consisting of propylene glycol, butylene glycol, glycerol, dipropylene glycol and octanediol.

[5] The composition of any one of the above-mentioned [1] to [4], further comprising an organic amine having 2-9 carbon atoms.

[6] The composition of the above-mentioned [5], wherein the organic amine having 2-9 carbon atoms is one or more kinds selected from the group consisting of monoethanolamine, monoisopropanolamine, diethanolamine, diisopropanolamine, triethanolamine, triisopropanolamine, ethylenediamine and tris(hydroxymethyl)aminomethane.

[7] The composition of the above-mentioned [5] or [6], wherein the composition is used for enhancing transdermal absorption of an acidic drug.

[8] The composition of any one of the above-mentioned [1] to [7], wherein the composition is used for a patch preparation.

[9] A patch preparation comprising a support and a drug-containing adhesive layer or a drug reservoir layer on one surface of the support, wherein each of the layers comprise the composition of any one of the above-mentioned [1] to [7] and a drug.

The present invention can achieve a composition for enhancing transdermal absorption of a drug, which can provide a sufficiently high enhancing effect on transdermal absorption of even a drug with poor transdermal absorbability.

In addition, a composition for enhancing transdermal absorption of a drug, which shows a more improved enhancing effect on transdermal absorption of, particularly, an acidic drug, can be realized by further combining an organic amine having 2-9 carbon atoms.

In addition, using the composition for enhancing transdermal absorption of a drug of the present invention, a matrix type or reservoir type patch preparation showing superior transdermal absorbability of a drug can be provided.

BRIEF DESCRIPTION OF THE DRAWINGS

In the Figures, 1 is a release liner, 2 is a drug-containing adhesive layer, 2' is an adhesive layer, 3 is a drug permeation control film, 4 is a drug reservoir layer, and is a support.

DESCRIPTION OF EMBODIMENTS

The present, invention is explained in the following by referring to the embodiments thereof.

The composition for enhancing transdermal absorption of a drug of the present invention (hereinafter to be also simply referred to as "the composition of the present invention") mainly comprises an unsaturated higher alcohol having 12-20 carbon atoms and a polyvalent alcohol having 3-8 carbon atoms.

As the unsaturated higher alcohol having 12-20 carbon atoms, a monovalent alcohol is generally used. The structure thereof is not particularly limited, and may be a linear or branched chain, preferably a linear chain. In addition, the number of unsaturated bonds may be one or more, preferably one or two. Specific examples include oleyl alcohol, trans-2-dodecenol, 2,4-dodecadien-1-ol, trans-2-tridecen-1-ol, trans-9-octadecenol, cis,cis-9,12-octadecadien-1-ol and the like. One or more kinds of such unsaturated higher alcohol having 12-20 carbon atoms can be used.

As the polyvalent alcohol having 3-8 carbon atoms (hereinafter to be also simply referred to as "polyvalent alcohol") a divalent or trivalent alcohol can be used, and the structure thereof is not particularly limited. Specific examples include propylene glycol, butylene glycol, glycerol, dipropylene glycol, octanediol and the like. Of these, one having 3-4 carbon atoms is preferable, and particularly preferred are propylene glycol and butylene glycol. One or more kinds of such polyvalent alcohol having 3-8 carbon atoms can be used.

The composition of the present invention can further contain an organic amine having 2-9 carbon atoms. The organic amine having 2-9 carbon atoms shows an action to increase solubility of a drug, particularly an acidic drug, in a preparation and the skin, and is advantageous for the transdermal absorbability of an acidic drug. As the organic amine having 2-9 carbon atoms, a primary, secondary or tertiary amine can be used. While the structure thereof is not particularly limited, monoethanolamine, monoisopropanolamine, diethanolamine, diisopropanolamine, triethanolamine, triisopropanolamine, ethylenediamine, tris(hydroxymethyl)aminomethane and the like are preferable. More preferred are diethanolamine, diisopropanolamine, triethanolamine, triisopropanolamine and the like.

The composition of the present invention can enhance transdermal absorption of various drugs. That is, a pharmaceutical composition superior in transdetiaal absorbability can be produced by combining a basic-compound to be used as an active ingredient of various pharmaceutical products or a salt thereof, and the composition of the present invention. The drug is not particularly limited as long as it has the property permitting administration via the skin of a mammal such as human and the like, i.e., transdermal absorbability. Specific examples include general anesthetics, hypnotic sedatives, antiepileptic drugs, antipyretic analgesic antiphlogistic drugs, anti-vertiginous drugs, psychoneurotic drugs, topical anesthetics, skeletal muscle relaxants, autonomic drugs, antispamodic drugs, anti-parkinsonian drugs, antihistamine drugs, cardiac stimulants, drugs for arrhythmia, diuretics, hypotensive drugs, vasoconstrictor, coronary vasodilators, peripheral vasodilators, arteriosclerosis drugs, drugs for circulatory organ, anapnoics, antitussive expectorants, hormone drugs, external drugs for purulent diseases, analgesic-antipruritic-styptic antiphogistic drugs, drugs for parasitic skin diseases, hemostatic drugs, drugs for treatment of gout, drugs for diabetes, antineoplastic drugs, antibiotics, chemical therapy drugs, narcotics, anti-schizophrenia drugs, antidepressants, quit smoking aids and the like.

The composition of the present invention containing an organic amine having 2-9 carbon atoms is particularly advantageous for the enhancement of transdermal absorption of an acidic drug. This is considered to be attributable to the action of the organic amine to remarkably improve the solubility of an acidic drug in a preparation and the skin. In the present invention, the "acidic drug" means a compound having an acidic functional group such as a carboxy group, a sulfo group, a thiol group, a phosphoric acid group, an aromatic hydroxyl group and the like in a molecule, which is used as an active ingredient of various pharmaceutical products, or a salt thereof, regardless of the presence or absence of a basic functional group in the molecule. When the acidic drug is particularly a compound having plural functional groups in a molecule, all of the plural functional groups are preferably acidic functional groups.

The "basic drug" means a compound having a basic functional group such as an amino group, an imino group and the like but having no acidic functional group in a molecule, which is used as an active ingredient of various pharmaceutical products, or a salt thereof. The "neutral drug" means a compound free of acidic functional group and basic functional group in a molecule, which is used as an active ingredient of various pharmaceutical products.

The content of each component in the composition of the present invention can be appropriately determined according to the kind of a drug desired to show enhanced transdermal absorption, desired transdermal absorption rate and the like. Generally, when the composition does not contain an organic amine, it is preferable that the amount of polyvalent alcohol in the total weight of polyvalent alcohol and higher alcohol (100 parts by weight) be about 50-99.99 parts by weight (preferably 80-99.9 parts by weight, more preferably 90-99.9 parts by weight, particularly preferably 95-99 parts by weight), with the rest being higher alcohol. When the composition contains an organic amine, it is preferable that the amount of polyvalent alcohol in the total weight of polyvalent alcohol, higher alcohol and organic amine (100 parts by weight) be about 40-99.9 parts by weight (preferably 50-99 parts by weight, more preferably 60-98 parts by weight, particularly preferably 90-97 parts by weight), and the rest being higher alcohol and organic amine. The mixing weight ratio of higher alcohol and organic amine (higher alcohol:organic amine) is preferably 0.01:99.99-99.99:0.01, more preferably 0.1:99.9-99.9:0.1, particularly preferably 1:99-99:1, most preferably 30:70-70:30.

The composition of the present invention is used for the preparation of a transdermal absorption preparation together with a drug. Examples of the dosage form of the transdermal absorption preparation include ointment, cream, liquid, lotion, liniment, poultice, emplastrum (plaster), adhesive preparation and the like. In many cases, the composition of the present invention is prepared into a drug-containing composition further contained a drug. From the aspect of enhancing effect on transdermal absorption of a drug, the content of the drug in the drug-containing composition is preferably a saturation concentration or not less than 80 wt % of the saturation concentration. Typically, 0.1-4.0 parts by weight, more preferably 0.5-35 parts by weight, particularly preferably 1.0-30 parts by weight, of a drug is preferably contained in the total amount of polyvalent alcohol and higher alcohol (100 parts by weight), or the total amount of polyvalent alcohol, higher alcohol and organic amine (100 parts by weight).

A patch preparation using the composition of the present invention is explained below.

The patch preparation of the present invention may be, what is called, a matrix type patch preparation having a drug-containing adhesive layer provided on one surface of a support or, what is called, a reservoir type patch preparation having an adhesive layer and a drug reservoir layer provided on one surface of a support.

<Matrix Type Patch Preparation>

Figure 1:
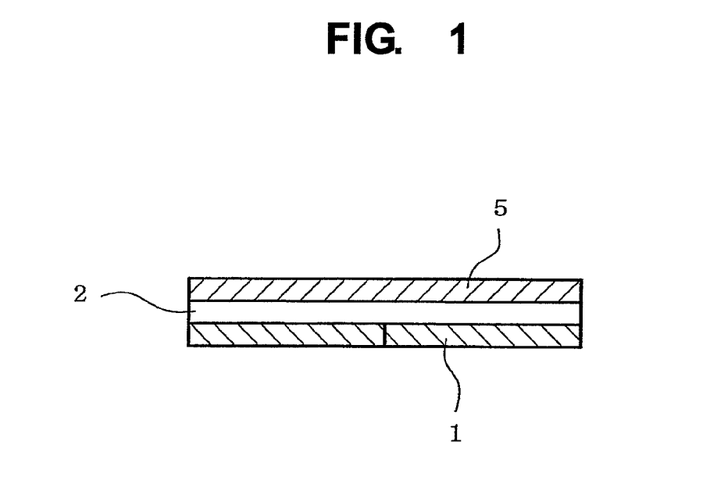
FIG. 1 is a schematic sectional view of one embodiment of the matrix type patch preparation of the present invention.

FIG. 1 shows a typical embodiment of a matrix type patch preparation, wherein a drug-containing adhesive layer (2) and a release liner (1) are laminated in this order on one surface of a support (5). In a matrix type patch preparation, a drug-containing adhesive layer containing the composition of the present invention is formed on one surface of a support.

The drug-containing adhesive layer can be formed through the following process: mixing the above-mentioned drug-containing composition prepared by adding a drug to the composition of the present invention, about 40-1900 wt % (preferably about 67-900 wt %) of an adhesive polymer based on the above-mentioned drug-containing composition and an adequate amount of a solvent to prepare a composition for forming an adhesive layer; applying the composition for forming an adhesive layer onto one surface of a support or a peel-treated surface of a release liner to form a laminate; and drying the laminate.

While the solvent is not particularly limited, ethyl acetate, toluene, hexane and the like are preferable. The drug-containing adhesive layer can be crosslinked and, in this case, a crosslinking agent can be further added to the composition for forming an adhesive layer. The composition for forming an adhesive layer can be applied to one surface of a support or release liner by, for example, casting, printing, and other technique known per se to those of ordinary skill in the art. After forming a drug-containing adhesive layer, a release liner or support is preferably adhered thereto for protection, preservation and the like of the drug-containing adhesive layer.

The above-mentioned adhesive polymer is not particularly limited, and acrylic polymer containing (meth)acrylic acid ester polymer; rubber polymer such as styrene-isoprene-styrene block copolymer, styrene-butadiene-styrene block copolymer, polyisoprene, polyisobutylene, polybutadiene and the like; silicone polymer such as silicone rubber, dimethylsiloxane base, diphenylsiloxane base and the like; vinyl ether polymer such as polyvinyl methyl ether, polyvinyl ethyl ether, polyvinyl isobutyl ether and the like; vinyl ester polymer such as vinyl acetate-ethylene copolymer and the like; ester polymer consisting of carboxylic acid component such as dimethyl terephthalate, dimethyl isophthalate, dimethyl phthalate and the like, and polyvalent alcohol component such as ethylene glycol and the like and the like can be mentioned. Of these, an acrylic polymer is preferable from the aspect of compatibility with polyvalent alcohol.

As an acrylic polymer, preferred is one obtained by copolymerization of (meth)acrylic acid alkyl ester as a main component and a functional monomer. That is, a copolymer comprising 50-99 wt % (preferably 60-95 wt %) of a monomer component consisting of (meth)acrylic acid alkyl ester, wherein the rest of the monomer component is a functional monomer, is preferable. The main component here means a monomer component contained in a proportion of not less than 50 wt % of the total weight of the monomer component constituting the copolymer.

The (meth)acrylic acid alkyl ester (hereinafter to be also referred to as the main component monomer) is generally that wherein the alkyl group is a straight chain or branched alkyl group having 4-13 carbon atoms (e.g., butyl, pentyl, hexyl, heptyl, 2-ethylhexyl, nonyl, decyl, undecyl, dodecyl, tridecyl and the like), and one or more kinds thereof are used.

The functional monomer has at least one unsaturated double bond, which is involved in a copolymerization reaction, in a molecule and a functional group on the side chain. Examples thereof include carboxyl group-containing monomer such as (meth)acrylic acid, itaconic acid, maleic acid, maleic anhydride and the like, hydroxyl group-containing monomer such as (meth)acrylic acid hydroxyethyl ester, (meth)acrylic acid hydroxypropyl ester and the like; sulfoxyl group-containing monomer such as styrene sulfonic acid, allyl sulfonic acid, sulfopropyl(meth)acrylate, (meth)acryloyloxynaphthalene sulfonic acid, acrylamide methylpropane sulfonic acid and the like; amino group-containing monomer such as (meth)acrylic acid aminoethyl ester, (meth)acrylic acid dimethylaminoethyl ester, (meth)acrylic acid tert-butylaminoethyl ester and the like; amide group-containing monomer such as (meth)acrylamide, dimethyl (meth)acrylamide, N-methylol(meth)acrylamide, N-methylolpropane(meth)acrylamide, N-vinylacetamido and the like; alkoxyl group-containing monomer such as (meth)acrylic acid methoxyethyl ester, (meth)acrylic acid ethoxyethyl ester, (meth)acrylic acid methoxyethylene glycol ester, (meth)acrylic acid methoxydiethylene glycol ester, (meth)acrylic acid methoxypolyethylene glycol ester, (meth)acrylic acid methoxypolypropylene glycol ester, (meth)acrylic acid tetrahydrofuryl ester and the like.

One or more kinds of such functional monomers can be used. Of those, a carboxyl group-containing monomer is preferable, and (meth)acrylic acid is particularly preferable from the aspects of pressure-sensitive adhesiveness of an adhesive layer, cohesiveness, releaseability of a drug contained in the adhesive layer and the like.

As the acrylic polymer, one obtained by further copolymerizing the above-mentioned copolymer of (meth)acrylic acid alkyl ester (main component monomer) and a functional monomer with other monomer can also be used.

Examples of such other monomer include (meth)acrylonitrile, vinyl acetate, vinyl propionate, N-vinyl-2-pyrrolidone, methylvinylpyrrolidone, vinylpyridine, vinylpiperidone, vinylpyrimidine, vinylpiperazine, vinylpyrrole, vinylimidazole, vinylcaprolactam, vinyloxazole and the like. One or more kinds of these can be used.

The amount of such other monomer to be used is generally preferably about 0-40 wt %, more preferably about 10-30 wt %, relative to the total weight of the (meth)acrylic acid alkyl ester (main component monomer) and the functional monomer.

As the acrylic polymer, a terpolymer of 2-ethylhexyl acrylate as (meth)acrylic acid alkyl ester, acrylic acid and N-vinyl-2-pyrrolidone is preferable, and a copolymer obtained by copolymerizing 2-ethylhexyl acrylate, acrylic acid and N-vinyl-2-pyrrolidone at a weight ratio of 40-99.8:0.1-10:0.1-50, preferably 50-89:1-8:10-40, is more preferable, since good adhesiveness to the human skin can be achieved, and adhesion and detachment can be easily repeated.

As the rubber polymer, one containing at least one kind selected from polyisobutylene, polyisoprene and styrene-diene-styrene block copolymer (styrene-butadiene-styrene block copolymer (SBS), styrene-isoprene-styrene block copolymer (SIS) etc.) as the main component is preferable. Since high drug stability, and necessary adhesive force and cohesion strength can be simultaneously achieved, a mixture of high molecular weight-polyisobutylene having a viscosity average molecular weight of 500,000-2,100,000, and low molecular weight-polyisobutylene having a viscosity average molecular weight of 10,000-200,000 at a weight ratio of 95:5-5:95 is particularly preferable.

The viscosity average molecular weight here is obtained by calculating the Staudinger index ($J_0$) according to the Schulz-Blaschke equation from the flow time of capillary of the Ubbelohde's viscometer at 20° C., and applying the $J_0$ value to the following equations.

$$J_o = \eta_{sp}/\{c(1+0.31\eta_{sp})\} \text{(Schulz-Blaschke equation)} \quad \text{[formula 1]} \quad \eta_{sp} = t/t_0 - 1$$

t: flow time of solution (according to Hagenbach-couette correction)
$t_0$: flow time of solvent (according to Hagenbach-couette correction)
c: concentration of solution (g/cm$^3$)
$J_0 = 3.06 \times 10^{-2}$ Mv$^{0.65}$
Mv: viscosity average molecular weight When a rubber polymer is used, it is preferable to further add a tackifier, since it can improve adhesiveness of a drug-containing adhesive layer at ambient temperature. The tackifier is not particularly limited, and those known in the technical field may be appropriately selected and used.

Examples thereof include petroleum resin (e.g., aromatic petroleum resin, aliphatic petroleum resin and the like), terpene resin, rosin resin, coumarone indene resin, styrene resin (e.g., styrene resin, poly(a-methylstyrene) and the like), hydrogenated petroleum resin (e.g., alicyclic saturated hydrocarbon resin and the like) and the like. Of these, an alicyclic saturated hydrocarbon resin is preferable, since the stability of the drug becomes fine. One or more kinds of tackifiers can be used in combination, and the amount of the tackifier is generally 33-300 wt %, preferably 50-200 wt %, relative to the total weight of the rubber polymer.

In the patch preparation of the present invention, the content of the composition for enhancing transdermal absorption of drug of the present invention in the drug-containing adhesive layer is preferably 5-70 wt %, more preferably 10-60 wt %, of the drug-containing adhesive layer as 100 wt %.

When desired, the drug-containing adhesive layer can further contain a plasticizer. The plasticizer is not particularly limited as long as it plasticizes the adhesive to confer a soft feeling to the adhesive layer, and reduce the pain and skin irritation caused by the skin adhesion force during detachment of the patch preparation from the skin. When a plasticizer is added to a drug-containing adhesive layer, it is added, together with the composition of the present invention, to a composition for foaming an adhesive layer during preparing of the composition. A plasticizer is preferably added in a proportion of 1-70 wt %, more preferably 20-60 wt %, of the drug-containing adhesive layer as 100 wt %.

Preferable examples of the plasticizer include fats and oils such as olive oil, castor oil, squalene, lanolin, organic solvents such as decylmethyl sulfoxide, methyloctyl sulfoxide, dimethyl sulfoxide, dimethylformamide, dimethylacetamide, methylpyrrolidone, dodecylpyrrolidone, surfactants such as polyoxyethylene sorbitan fatty acid ester, sorbitan ester of fatty acid, polyoxyethylene fatty acid ester, phthalic acid esters such as dibutyl phthalate, diheptyl phthalate, dioctyl phthalate and the like, sebacic acid esters such as diethyl sebacate, dibutyl sebacate, dioctyl sebacate and the like, hydrocarbons such as liquid paraffin, fatty acid esters such as ethyl oleate, diisopropyl adipate, isopropyl palmitate, octyl palmitate, isopropyl myristate, isotridecyl myristate, ethyl laurate and the like, fatty acid ester of glycerin, propylene glycol fatty acid ester, ethoxylated stearyl alcohol, pyrrolidone carboxylic acid fatty acid ester and the like. Any one kind of these may be used alone, or two or more kinds thereof may be used in combination.

A crosslinking structure can be introduced into the drug-containing adhesive layer. For this end, the drug-containing adhesive layer can be subjected to a physical crosslinking treatment by irradiation such as UV irradiation, electron beam irradiation and the like, or a chemical crosslinking treatment using various crosslinking agents such as isocyanate compounds (e.g., trifunctional isocyanates and the like), organic peroxide, organometallic salt, metal alcoholate, metal chelate compound, polyfunctional compound (polyfunctional external crosslinking agents and polyfunctional monomers for internal crosslinking such as diacrylate, dimethacrylate and the like) and the like. When a chemical crosslinking treatment is performed, a crosslinking agent is added, together with the composition of the present invention, to a composition for forming an adhesive layer, the composition for forming an adhesive layer is applied to one surface of a support or a peel-treated surface of a release liner and dried to form a drug-containing adhesive layer, the release liner or support is adhered onto the drug-containing adhesive layer, and the laminate is left standing at 60-90° C., preferably 60-70° C., for 24-48 hr to enhance the crosslinking reaction, whereby a drug-containing adhesive layer having a crosslinking structure is formed.

In the patch preparation of the present invention, while the thickness of the drug-containing adhesive layer is not particularly limited, it is preferably 20-300 μm, more preferably 30-300 μm, most preferably 50-300 μm. When the thickness of the adhesive layer is less than 20 μm, it may be difficult to obtain sufficient adhesive force and contain an effective amount of a drug. When the thickness of the adhesive layer exceeds 300 μm, formation of an adhesive layer may become difficult (difficulty of coating).

While the support is not particularly limited, it is specifically, for example, a single film such as polyester (e.g., poly(ethylene terephthalate) (PET) etc.), nylon, polyvinyl chloride, polyethylene, polypropylene, ethylene-vinyl acetate copolymer, polytetrafluoroethylene, ionomer resin and the like, metal foil, or a laminate film of two or more kinds of films selected therefrom and the like. To improve adhesiveness (anchor property) of a support to an adhesive layer, the support is preferably a laminate film of a non-porous film comprised of the above-mentioned material and a porous film mentioned below, and an adhesive layer is preferably formed on the side of the porous film. The thickness of the non-porous film is preferably 2-100 μm, more preferably 2-50 μm.

The porous film is not particularly limited as long as it improves the anchor property to an adhesive layer and, for example, paper, woven fabric, non-woven fabric (e.g., polyester (e.g., poly(ethylene terephthalate) (PET) and the like) non-woven fabric and the like), the above-mentioned film with mechanical perforation (e.g., single films such as polyester, nylon, Saran (trade name), polyethylene, polypropylene, ethylene-vinyl acetate copolymer, polyvinyl chloride, ethylene-ethyl acrylate copolymer, polytetrafluoroethylene, metal foil, poly(ethylene terephthalate) and the like, and a laminate film by laminating one or more kinds of these and the like) and the like can be mentioned. Particularly, paper, woven fabric and non-woven fabric (e.g., polyester non-woven fabric, poly(ethylene terephthalate) non-woven fabric and the like) are preferable to afford flexibility of the support. When a porous film, for example, woven fabric or non-woven fabric is used, the weight thereof is preferably 5-30 g/m$^2$ to improve the anchor property.

The laminate film as a support is produced by a known production method of a laminate film such as dry lamination method, wet lamination method, extrusion lamination method, hot melt lamination method, coextrusion lamination method and the like.

While the thickness of the support is not particularly limited, it is preferably 2-200 μm, more preferably 10-50 μm. When it is less than 2 μm, handling property such as self-supporting property and the like tends to decrease, and when it exceeds 200 μm, an unpleasant feeling (a feeling of stiffness) is produced to often degrade the followability.

Examples of the release liner include a release liner having a peel-treated layer comprised of a peel-treating agent, which is formed on the surface of a substrate for a release liner, a plastic film having high detachability in itself, a release liner having a release layer comprised of the aforementioned plastic film having high detachability, which is formed on the surface of a substrate for release liner and the like. The release surface of the release liner may be only one surface of the substrate or both surfaces thereof.

In such release liner, the peel-treating agent is not particularly limited and examples thereof include release agents such as long-chain alkyl group-containing polymer, silicone polymer (silicone release agent), fluorine polymer (fluorine release agent) and the like. Examples of the substrate for a release liner include plastic films such as poly(ethylene terephthalate) (PET) film, polyimide film, polypropylene film, polyethylene film, polycarbonate film, polyester (excluding PET) film and the like and metal vapor-deposited plastic film obtained by vapor deposition of a metal on these films; papers such as Japanese paper, foreign paper, craft paper, glassine, quality paper and the like; substrates made from a fibrous material such as non-woven fabric, fabric and the like; metal foil and the like.

Examples of the plastic film having high detachability in itself include ethylene-a-olefin copolymers (block copolymer or random copolymer) such as polyethylene (low density polyethylene, linear low density polyethylene etc.), polypropylene, ethylene-propylene copolymer and the like, polyolefin film made of a polyolefin resin comprised of a mixture thereof; Teflon (registered trade mark) film and the like.

A release layer on the surface of the aforementioned substrate for a release liner can be foisted by laminating or coating a material of the aforementioned plastic film having high detachability on the aforementioned substrate for a release liner.

While thickness (total thickness) of the release liner is not particularly limited, it is generally not more than 200 μm, preferably 25-100 μm.

<Reservoir Type Patch Preparation>

Figure 2:
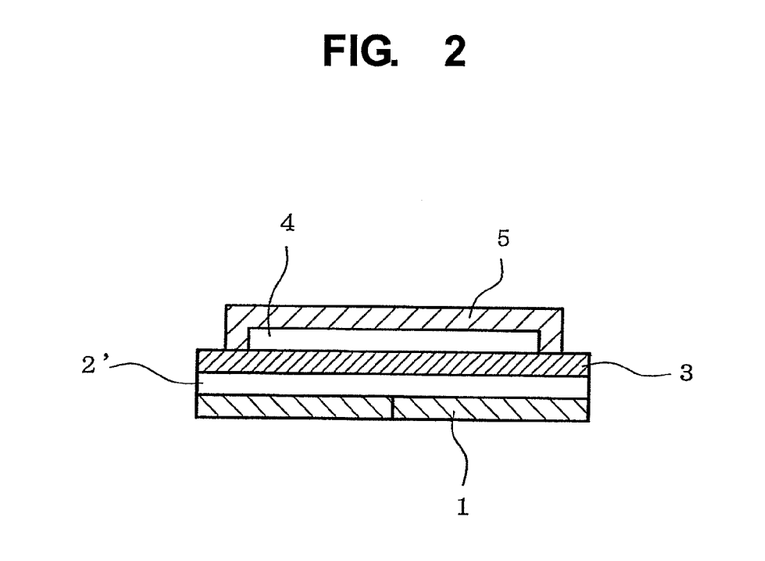
FIG. 2 is a schematic sectional view of one embodiment of the reservoir type patch preparation of the present invention.

FIG. 2 shows a typical example of a reservoir type patch preparation, wherein a drug reservoir layer (4), a drug permeation control film (3), an adhesive layer (2'), and a release liner (1) are laminated in this order on one surface of a support (5).

In a reservoir type patch preparation the composition of the present invention is generally used for a drug reservoir layer. That is, a drug is added to the composition of the present invention to give a drug-containing composition, which is applied to a drug reservoir layer. The drug-containing composition can further contain a drug stabilizer, a gelling agent and the like. In addition, it can also be applied to a drug reservoir layer by impregnating a non-woven fabric and the like with a drug-containing composition.

The materials, thickness etc. to be used for support (5) and release liner (1) are basically the same as those of the aforementioned matrix type patch preparation. As a drug permeation control film (3), a micro pore film having an average pore size of 0.1-1 μm can be mentioned. As a material for the micro pore film, polyolefin such as polypropylene, polyethylene and the like, polytetrafluoroethylene and the like are used. While the thickness of the drug permeation control film is generally 1 μm-200 μm, it is desirably 10 μm-100 μm particularly from the aspects of easiness of production, appropriate stiffness and the like.

EXAMPLES

The present invention is explained in more detail in the following by referring to Examples and Comparative Examples, which are not to be construed as limitative. In the following description, parts or % means parts by weight or wt %.

<Preparation of Composition for Enhancing Transdermal Absorption of a Drug>

Examples 1-6 and Comparative Examples 1-11

The starting materials in the amounts shown in Table 1 were blended, a drug in an amount of a saturation concentration or above was further added, and the mixture was thoroughly stirred and filtered through a polytetrafluoroethylene (PTFE) disposable filter with pore size 0.45 μm to give a drug-containing composition for patch preparation, which contained the drug at a saturation concentration. As the drug, indomethacin, which is an acidic drug, was used. In the Table, the unit of the numbers is parts by weight.

TABLE 1

|  | PG | SA | ISA | OA | MEA | DEA | DIPA | TEA | TIPA | IND |
|---|---|---|---|---|---|---|---|---|---|---|
| Ex. 1 | 98 |  |  | 2 |  |  |  |  |  | saturated |
| Ex. 2 | 96 |  |  | 2 |  |  | 2 |  |  | saturated |
| Ex. 3 | 96 |  |  | 2 | 2 |  |  |  |  | saturated |
| Ex. 4 | 96 |  |  | 2 |  | 2 |  |  |  | saturated |
| Ex. 5 | 96 |  |  | 2 |  |  |  | 2 |  | saturated |
| Ex. 6 | 96 |  |  | 2 |  |  |  |  | 2 | saturated |
| Comp. Ex. 1 | 98 | 2 |  |  |  |  |  |  |  | saturated |
| Comp. Ex. 2 | 98 |  | 2 |  |  |  |  |  |  | saturated |

TABLE 1-continued

|  | PG | SA | ISA | OA | MEA | DEA | DIPA | TEA | TIPA | IND |
|---|---|---|---|---|---|---|---|---|---|---|
| Comp. Ex. 3 | 96 | 2 |  |  |  |  | 2 |  |  | saturated |
| Comp. Ex. 4 | 100 |  |  |  |  |  |  |  |  | saturated |
| Comp. Ex. 5 |  |  | 100 |  |  |  |  |  |  | saturated |
| Comp. Ex. 6 |  |  |  | 100 |  |  |  |  |  | saturated |
| Comp. Ex. 7 | 98 |  |  |  | 2 |  |  |  |  | saturated |
| Comp. Ex. 8 | 98 |  |  |  |  | 2 |  |  |  | saturated |
| Comp. Ex. 9 | 98 |  |  |  |  |  | 2 |  |  | saturated |
| Comp. Ex. 10 | 98 |  |  |  |  |  |  | 2 |  | saturated |
| Comp. Ex. 11 | 98 |  |  |  |  |  |  |  | 2 | saturated |

The abbreviations in Table 1 mean as follows. PG: propylene glycol, LA: lauryl alcohol, ISA: isostearyl alcohol, OA: oleyl alcohol, MEA: monoethanolamine, DEA: diethanolamine, DIPA: diisopropanolamine, TEA: triethanolamine, TIPA: triisopropanolamine, IND: indomethacin To evaluate the skin permeability of indomethacin in Examples 1-6 and Comparative Examples 1-11, the following test (Experimental Example 1) was conducted. Table 2 shows the results thereof.

Experimental Example 1

Skin Permeability Test

The skin isolated from a hairless mouse was mounted on a cell for skin permeation experiment (effective area 9 mmφ) such that the stratum corneum side was a donor phase and the corium side was a receptor phase, a composition for enhancing transdermal absorption of a drug (127 µL) containing a drug was added from to upper part and a skin permeation experiment was conducted for 24 hr. As a receptor solution, a deaerated PBS(−) solution (phosphate buffered saline) was used. The receptor solution was sampled over time and the concentration of the permeated drug was quantified by HPLC (high performance liquid chromatography).

TABLE 2

|  | 8 hr accumulated permeation amount (µg/cm²/8 h) | 24 hr accumulated permeation amount (µg/cm²/24 h) |
|---|---|---|
| Ex. 1 | 643.42 | 1826.33 |
| Ex. 2 | 869.97 | 4842.33 |
| Ex. 3 | 636.61 | 3187.64 |
| Ex. 4 | 1187.03 | 6287.47 |
| Ex. 5 | 1109.44 | 4587.85 |
| Ex. 6 | 839.03 | 3366.34 |
| Comp. Ex. 1 | 19.33 | 2415.06 |
| Comp. Ex. 2 | 134.13 | 673.72 |
| Comp. Ex. 3 | 234.91 | 1581.73 |
| Comp. Ex. 4 | 0 | 30.31 |
| Comp. Ex. 5 | 9.07 | 67.64 |
| Comp. Ex. 6 | 10.83 | 68.41 |
| Comp. Ex. 7 | 2.49 | 272.47 |
| Comp. Ex. 8 | 14.12 | 66.29 |
| Comp. Ex. 9 | 0.31 | 274.4 |
| Comp. Ex. 10 | 1.11 | 17.56 |
| Comp. Ex. 11 | 1.78 | 341.01 |

In Table 2, by comparison of Example 1 and Comparative Examples 4, 6, the permeability of the drug was very low in Comparative Example 4 using only propylene glycol, which is a polyvalent alcohol, and Comparative Example 6 using only oleyl alcohol, which is an unsaturated higher alcohol, but markedly increased in Example 1 using propylene glycol and oleyl alcohol in combination as compared to Comparative Examples 4, 6, where the enhancing effect on transdermal absorption of a drug by the combination was synergistic.

From these results, it has been clarified that the combination of propylene glycol, which is a polyvalent alcohol, and oleyl alcohol, which is an unsaturated higher alcohol, markedly enahnces transdermal permeability of an acidic drug.

By comparison of Example 2 and Comparative Examples 4, 6, 9, the permeability of the drug was very low in Comparative Example 4 using only propylene glycol, which is a polyvalent alcohol, and Comparative Example 6 using only oleyl alcohol, which is an unsaturated higher alcohol, but enhanced in Comparative Example 9 using propylene glycol and diisopropanolamine, which is an organic amine, in combination as compared to Comparative Examples 4, 6. In Example 2 using propylene glycol, oleyl alcohol and diisopropanolamine in combination, the permeability of the drug further increased markedly, where the enhancing effect on transdermal absorption of a drug by the combination was synergistic.

By comparison of Example 3 and Comparative Examples 4, 6, 7, the permeability of the drug was very low in Comparative Example 4 using only propylene glycol, which is a polyvalent alcohol, and Comparative Example 6 using only oleyl alcohol, which is an unsaturated higher alcohol, but enhanced in Comparative Example 7 using propylene glycol and monoethanolamine, which is an organic amine, in combination as compared to Comparative Examples 4, 6. In Example 3 using propylene glycol, oleyl alcohol and monoethanolamine in combination, the permeability of the drug further increased markedly, where the enhancing effect on transdermal absorption of a drug by the combination was synergistic.

By comparison of Example 4 and Comparative Examples 4, 6, 8, the permeability of the drug was very low in Comparative Example 4 using only propylene glycol, which is a polyvalent alcohol, and Comparative Example 6 using only oleyl alcohol, which is an unsaturated higher alcohol, but enhanced in Comparative Example 8 using propylene glycol and diethanolamine, which is an organic amine, in combination as compared to Comparative Examples 4, 6. In Example 4 using propylene glycol, oleyl alcohol and diethanolamine in combination, the permeability of the drug further increased markedly, where the enhancing effect on transdermal absorption of a drug by the combination was synergistic.

By comparison of Example 5 and Comparative Examples 4, 6, 10, the permeability of the drug was very low in Comparative Example 4 using only propylene glycol, which is a polyvalent alcohol, and Comparative Example 6 using only oleyl alcohol, which is an unsaturated higher alcohol, but enhanced in Comparative Example 10 using propylene glycol and triethanolamine, which is an organic amine, in combination as compared to Comparative Examples 4, 6. In Example 5 using propylene glycol, oleyl alcohol and triethanolamine in combination, the permeability of the drug further increased markedly, where the enhancing effect on transdermal absorption of a drug by the combination was synergistic.

By comparison of Example 6 and Comparative Examples 4, 6, 11, the permeability of the drug was very low in Comparative Example 4 using only propylene glycol, which is a polyvalent alcohol, and Comparative Example 6 using only oleyl alcohol, which is an unsaturated higher alcohol, but enhanced in Comparative Example 11 using propylene glycol and triisopropanolamine, which is an organic amine, in combination as compared to Comparative Examples 4, 6. In Example 6 using propylene glycol, oleyl alcohol and triisopropanolamine in combination, the permeability of the drug further increased markedly, where the enhancing effect on transdermal absorption of a drug by the combination was synergistic.

From the above results, it has been clarified that the combination of polyvalent alcohol, unsaturated higher alcohol and organic amine markedly enhances transdermal permeability of an acidic drug.

Example 7 and Comparative Examples 12, 13

The starting materials in the amounts shown in Table 3 were blended, a drug in an amount of a saturation concentration or above was further added, and the mixture was thoroughly stirred and filtered through a polytetrafluoroethylene (PTFE) disposable filter with pore size 0.45 μm to give a composition for enhancing transdermal absorption, which contained the drug at a saturation concentration. As the drug, valsartan, which is an acidic drug, was used. In the Table, the unit of the numbers is parts by weight.

TABLE 3

|  | PG | OA | DIPA | VAL |
|---|---|---|---|---|
| Ex. 7 | 96 | 2 | 2 | saturated |
| Comp. Ex. 12 | 100 |  |  | saturated |
| Comp. Ex. 13 | 98 |  | 2 | saturated |

Note)
PG: propylene glycol, OA: oleyl alcohol, DIPA: diisopropanolamine, VAL: valsartan The compositions of Example 7 and Comparative Examples 12, 13, which contain valsartan at a saturation concentration, were subjected to a skin permeability test similar to that in the aforementioned Experimental Example 1. Table 4 shows the results thereof.

TABLE 4

|  | 8 hr accumulated permeation amount ($\mu g/cm^2/8$ h) | 24 hr accumulated permeation amount ($\mu g/cm^2/24$ h) |
|---|---|---|
| Ex. 7 | 310.92 | 1564.86 |
| Comp. Ex. 12 | 0 | 4.25 |
| Comp. Ex. 13 | 0 | 9.35 |

By comparison of Example 7 and Comparative Examples 12, 13, the permeability of the drug was very low in Comparative Example 12 using only propylene glycol, which is a polyvalent alcohol, but, somewhat enahnced in Comparative Example 13 using propylene glycol and diisopropanolamine, which is an organic amine, in combination as compared to Comparative Example 12. In contrast, in Example 7 using propylene glycol, oleyl alcohol, which is an unsaturated higher alcohol, and diisopropanolamine, which is an organic amine, in combination, the permeability of the drug increased markedly, where the enhancing effect on transdermal absorption of a drug by the combination was synergistic.

Examples 8, 9 and Comparative Examples 14, 15

The starting materials in the amounts shown in Table 5 were blended, a drug in an amount of a saturation concentration or above was further blended, and the mixture was thoroughly stirred and filtered through a polytetrafluoroethylene (PTFE) disposable filter with pore size 0.45 μm to give a composition for enhancing transdermal absorption of a drug, which contained the drug at a saturation concentration. As the drug, zolmitriptan, which is a basic drug, was used. In the Table, the unit of the numbers is parts by weight.

TABLE 5

|  | PG | OA | DIPA | ZLM |
|---|---|---|---|---|
| Comp. Ex. 14 | 100 |  |  | saturated |
| Comp. Ex. 15 | 98 |  | 2 | saturated |
| Ex. 8 | 98 | 2 |  | saturated |
| Ex. 9 | 96 | 2 | 2 | saturated |

Note)
PG: propylene glycol, OA: oleyl alcohol, DIPA: diisopropanolamine, ZLM: zolmitriptan The compositions of Examples 8, 9 and Comparative Examples 14, 15, which contain zolmitriptan at a saturation concentration, were subjected to a skin permeability test similar to that in the aforementioned Experimental Example 1. Table 6 shows the results thereof.

TABLE 6

|  | 8 hr accumulated permeation amount ($\mu g/cm^2/8$ h) | 24 hr accumulated permeation amount ($\mu g/cm^2/24$ h) |
|---|---|---|
| Comp. Ex. 14 | 0.35 | 9.03 |
| Comp. Ex. 15 | 0.4 | 6.72 |
| Ex. 8 | 366.76 | 2185.14 |
| Ex. 9 | 268.17 | 1615.29 |

From Table 6, as compared to Comparative Example 14 using only propylene glycol and Comparative Example 15 using propylene glycol and diisopropanolamine, which is an organic amine, in combination, the permeability of the drug increased markedly in Example 8 using propylene glycol and oleyl alcohol, which is an unsaturated higher alcohol, in combination and Example 9 using propylene glycol, oleyl alcohol, which is an unsaturated higher alcohol, and diisopropanolamine, which is an organic amine, in combination. However, Example 9 showed somewhat lower drug permeability than Example 8, from which it has been found that application of a composition containing polyvalent alcohol, unsaturated higher alcohol and organic amine in combination to a basic drug does not provide a remarkable drug permeability-improving effect attributable to the combination with an organic amine, unlike the application thereof to an acidic drug.

Examples 10, 11 and Comparative Examples 16, 17

The starting materials in the amounts shown in Table 7 were blended, a drug in an amount of a saturation concentration or above was further blended, and the mixture was thoroughly stirred and filtered through a polytetrafluoroethylene (PTFE) disposable filter with pore size 0.45 µm to give a composition for enhancing transdermal absorption of a drug, which contained the drug at a saturation concentration. As the drug, estradiol, which is a neutral drug, was used. In the Table, the unit of the numbers is parts by weight.

TABLE 7

|  | PG | OA | DIPA | EST |
|---|---|---|---|---|
| Comp. Ex. 16 | 100 |  |  | saturated |
| Comp. Ex. 17 | 98 |  | 2 | saturated |
| Ex. 10 | 98 | 2 |  | saturated |
| Ex. 11 | 96 | 2 | 2 | saturated |

Note)
PG: propylene glycol, OA: oleyl alcohol, DIPA: diisopropanolamine, EST: estradiol The compositions of Examples 10, 11 and Comparative Examples 16, 17, which contain estradiol at a saturation concentration, were subjected to a skin permeability test similar to that in the aforementioned Experimental Example 1. Table 8 shows the results thereof.

TABLE 8

|  | 8 hr accumulated permeation amount (µg/cm$^2$/8 h) | 24 hr accumulated permeation amount (µg/cm$^2$/24 h) |
|---|---|---|
| Comp. Ex. 16 | 2.27 | 26.19 |
| Comp. Ex. 17 | 2.05 | 8.67 |
| Ex. 10 | 13.64 | 29.56 |
| Ex. 11 | 15.69 | 27.48 |

From Table 8, as compared to Comparative Example 16 using only propylene glycol and Comparative Example 17 using propylene glycol and diisopropanolamine, which is an organic amine, in combination, the peimeability of the drug increased in Example 10 using propylene glycol and oleyl alcohol, which is an unsaturated higher alcohol, in combination and Example 11 using propylene glycol, oleyl alcohol, which is an unsaturated higher alcohol, and diisopropanolamine, which is an organic amine, in combination. However, the permeability of Example 10 and Example 11 was equivalent, from which it has been found that application of a composition containing polyvalent alcohol, unsaturated higher alcohol and organic amine in combination to a neutral drug does not provide a remarkable drug permeability-improving effect attributable to the combination with an organic amine, unlike the application thereof to an acidic drug.

<Formulation of Patch Preparation>

Example 12

(1) Preparation of Acrylic Polymer Solution

Under an inert gas atmosphere, 2-ethylhexyl acrylate (75 parts), N-vinyl-2-pyrrolidone (22 parts), acrylic acid (3 parts) and azobisisobutyronitrile (0.2 part) were added to ethyl acetate, solution polymerization was performed at 60° C. to give an acrylic polymer solution (polymer solid content: 28%).

(2) Formulation of acrylic patch preparation

To the above-mentioned composition for enhancing transdermal absorption of a drug of the present invention (30 parts), which contains the drug, are added an acrylic polymer solution in an amount to achieve a polymer solid content of 49.7 parts, isopropyl myristate (20 parts), and 0.3 part of a crosslinking agent, and the mixture is thoroughly stirred to give a composition (coating solution) for forming an adhesive layer. This is applied to one surface of a poly(ethylene terephthalate) (hereinafter to be referred to as PET) film (thickness 75 µm) as a release liner such that the thickness after drying is 200 µm, and dried to form an adhesive layer.

To the adhesive layer is adhered a non-woven fabric surface of a PET film (thickness 2 µm)-PET non-woven fabric (fabric weight 12 g/m$^2$) laminate as a support, and the laminate is subjected to an ageing treatment (crosslinking treatment of adhesive layer) at 70° C. for 48 hr to give a laminate sheet. The laminate sheet is cut into a shape of a patch preparation, and packed in a package container in an atmosphere with an oxygen concentration of 3% or below to give a patch preparation.

Since the composition of the present invention can increase the transdermal absorbability of a drug, particularly an acidic drug, a transdermal absorption preparation of a drug, particularly an acidic drug, which has heretofore been difficult to formulate due to its low transdermal absorbability, can be formulated by applying the composition of the present invention.

This application is based on a patent application No. 2011-200023 filed in Japan, the contents of which are incorporated in full herein.

The invention claimed is:

1. A composition for enhancing transdermal absorption of a drug, consisting of an unsaturated higher alcohol having 12-20 carbon atoms, propylene glycol, and an organic amine having 2-9 carbon atoms,
    wherein the amount of the propylene glycol relative to 100 parts by weight of the total weight of the propylene glycol, the unsaturated higher alcohol and the organic amine is 90-97 parts by weight.

2. The composition according to claim 1, wherein the unsaturated higher alcohol having 12-20 carbon atoms is a straight chain alcohol.

3. The composition according to claim 1, wherein the unsaturated higher alcohol having 12-20 carbon atoms contains oleyl alcohol.

4. The composition according to claim 1, wherein the organic amine having 2-9 carbon atoms is at least one selected from the group consisting of monoethanolamine, monoisopropanolamine, diethanolamine, diisopropanolamine, triethanolamine, triisopropanolamine, ethylenediamine and tris(hydroxymethyl)aminomethane.

5. The composition according to claim 1, wherein the composition is used for enhancing transdermal absorption of an acidic drug.

6. The composition according to claim 1, wherein the composition is used for a patch preparation.

7. A patch preparation comprising a support and a drug-containing adhesive layer or a drug reservoir layer on one surface of the support, wherein each of the layers comprise the composition according to claim 1 and a drug.

8. A composition fir enhancing transdermal absorption of a drug, consisting of oleyl alcohol, propylene glycol, and diisopropanolamine,
    wherein the amount of the propylene glycol relative to 100 parts by weight of the total weight of the propylene glycol, the oleyl alcohol and diisoproponalomaine is 90-97 part by weight.

* * * * *